(12) United States Patent
Sigrist et al.

(10) Patent No.: US 9,629,957 B2
(45) Date of Patent: Apr. 25, 2017

(54) AMBULATORY INSULIN INFUSION SYSTEM WITH BOLUS ADMINISTRATION DELAY

(75) Inventors: Reto Sigrist, Golaten (CH); Nicole Bernini, Burgdorf (CH); Axel Remde, Luetzelflueh (DE)

(73) Assignee: Roche Diagnostics International AG, Steinhausen (CH)

( * ) Notice: Subject to any disclaimer, the term of this patent is extended or adjusted under 35 U.S.C. 154(b) by 1454 days.

(21) Appl. No.: 12/969,664

(22) Filed: Dec. 16, 2010

(65) Prior Publication Data

US 2011/0160695 A1     Jun. 30, 2011

(30) Foreign Application Priority Data

Dec. 28, 2009  (EP) ..................................... 09016040

(51) Int. Cl.
*A61M 5/142*     (2006.01)
*A61M 5/172*     (2006.01)

(52) U.S. Cl.
CPC ...... *A61M 5/14248* (2013.01); *A61M 5/1723* (2013.01)

(58) Field of Classification Search
CPC ......................... A61M 5/14248; A61M 5/1723
USPC .......................................... 604/890.1, 65–67
See application file for complete search history.

(56) References Cited

U.S. PATENT DOCUMENTS

| | | | |
|---|---|---|---|
| 6,554,798 B1* | 4/2003 | Mann et al. | 604/131 |
| 7,344,500 B2* | 3/2008 | Talbot et al. | 600/365 |
| 2007/0156177 A1* | 7/2007 | Harel et al. | 607/1 |
| 2008/0125701 A1 | 5/2008 | Moberg et al. | |
| 2009/0177147 A1 | 7/2009 | Blomquist et al. | |

FOREIGN PATENT DOCUMENTS

| | | |
|---|---|---|
| WO | 03053498 A2 | 7/2003 |
| WO | 2007056592 A2 | 5/2007 |

OTHER PUBLICATIONS

European Search Report, Application No. EP 09 01 6040.9 filed Dec. 28, 2009, completion date of Jun. 11, 2010, pp. 1-5.

* cited by examiner

*Primary Examiner* — Bradley Osinski
(74) *Attorney, Agent, or Firm* — Dinsmore & Shohl LLP

(57) ABSTRACT

In one embodiment, an ambulatory insulin infusion system may include an administration module for insulin administration, a data collection module for collecting data relevant for the bolus amount, and a delay module. The administration module may administer insulin continuously according to a basal profile and a bolus on demand. The bolus has a bolus amount. The data collection module may be operatively coupled to the administration module. The delay module may trigger administration of the bolus a therapeutically significant delay interval after the data is collected.

18 Claims, 4 Drawing Sheets

AMBULATORY INSULIN INFUSION SYSTEM WITH BOLUS ADMINISTRATION DELAY

CROSS REFERENCE TO RELATED APPLICATIONS

The present application claims priority to European Patent Application No. EP09016040 filed Dec. 28, 2009.

TECHNICAL FIELD

The embodiments described herein generally relate to ambulatory insulin infusion systems and, more specifically, to ambulatory insulin infusion systems as used in the therapy of Diabetes Mellitus by continuous subcutaneous insulin infusion.

BACKGROUND

Ambulatory insulin infusion systems may be used for the therapy of Diabetes Mellitus. Ambulatory insulin infusion systems may include an insulin pump designed to be carried by a Person with Diabetes (hereinafter PwD) substantially continuously night and day. Ambulatory insulin infusion systems may to administer insulin into the PwD's subcutaneous tissue via a subcutaneous cannula, which can be replaced by the PwD every few days. Insulin pumps commonly administer insulin according to a basal administration profile which is typically pre-programmed and varies over the time of day. In addition, insulin pumps can be designed to administer larger insulin boli on demand, e.g., to compensate for the intake of food comprising carbohydrates and to lower undesirably raised blood glucose values. An insulin pump is disclosed, for example, in WO 2003053498 A2 to which reference is made for a typical design and typical features of such devices.

Discreetness of an ambulatory infusion system is a factor for the acceptance of continuous subcutaneous insulin infusion by many PwDs who may want to draw minimal attention, if any, towards their disease. Therefore, insulin pumps are designed to be carried in a concealed manner, e.g. in a trousers pocket, in a holster at a belt or as adhesive patch which is directly attached to the skin. The achievable discreetness for operating and programming the devices, however, may be limited. The devices are often coupled to a subcutaneous cannula via infusion tubing and carried at locations where they are not easily accessible. A meal bolus may be programmed prior to a meal, which may involve measuring a blood glucose value in a public environment. Therefore, meal bolus programming may impact the discreetness of an ambulatory infusion system.

A typical procedure for programming a bolus is described in the following for a commercially available system. The system allows comparatively discreet operation because it includes, in addition to an insulin pump, a separate diabetes manager with an integrated blood glucose measurement module that allows control over most functions of the pump wirelessly via a radio frequency (hereinafter RF) interface. The diabetes manager has a similar physical appearance (i.e., size and look) to a cell phone. Insulin pumps are generally substantially smaller in size and accordingly only provides a limited user interface, i.e., the diabetes manager provides a larger and more comfortable user interface. It can accordingly be operated in a comparatively discrete and convenient way.

When a PwD intends to take a meal, the following steps (A)-(D) are typically performed:

(A) Taking a blood glucose measurement. This includes the sub-steps of (i) removing a test strip from a container; (ii) placing the test strip in a corresponding socket of the diabetes manager, thus switching the device on; (iii) piercing the skin with a lancet or piercing device; (iv) placing a drop of blood on a corresponding section of the test strip; (v) reading the measured blood glucose value from a display; and (vi) removing and disposing the used test strip.

(B) Marking the measured blood glucose value. For this purpose, the diabetes manager may offer a list of situations such as, for example, "before meal", "after meal", "before sports," and the like. An item from the situations may be selected via keys. While this step is optional, it adds information for diary keeping and evaluation purposes. The information may also be considered in the subsequent step of determining the insulin bolus amount.

(C) Entering the carbohydrate amount of the meal the PwD intends to eat. Alternatively, a meal may be selected from a food database of the diabetes manager. Based on the blood glucose value and the carbohydrate amount, the diabetes manager calculates an appropriate insulin bolus amount for the current time of day. For this purpose, a number of algorithms are known in the art, such as disclosed in the WO 2006/066926.

(D) The calculated bolus amount is displayed on the display of the diabetes manager and is confirmed by the PwD. Optionally, a further step may be carried out in which an appropriate administration profile over time is selected from a list for taking into account the carbohydrate absorption characteristics of different meals.

After a final confirmation by the PwD, the bolus amount is transmitted to the insulin pump which subsequently administers the bolus.

Depending on the specific system, the details and the sequence of the may vary. The above example is provided to illustrate a general procedure for programming a bolus without limiting the embodiments described herein.

As should now be apparent, programming a bolus may be difficult to perform discretely in a number of situations. For example, in a public restaurant or the like, the PwD may not be able to pierce the skin and place a drop of blood on a test strip without drawing undesired interest from others. Furthermore, in some cases, carrying the diabetes manager is inconvenient during mealtime and directly operating the insulin pump is indiscreet and/or uncomfortable when carried concealed from view.

Accordingly, a need exists for alternative ambulatory insulin infusion systems that can be conveniently and discretely operated.

SUMMARY

In one embodiment, an ambulatory insulin infusion system may include an administration module for insulin administration, a data collection module for collecting data relevant for the bolus amount, and a delay module. The administration module may administer insulin continuously according to a basal profile and a bolus on demand. The bolus has a bolus amount. The data collection module may be operatively coupled to the administration module. The delay module may trigger administration of the bolus a therapeutically significant delay interval after the data is collected.

In another embodiment, an ambulatory insulin infusion system may include an administration module for insulin administration, a data collection module for collecting data relevant for the bolus amount, a delay module that starts a therapeutically significant delay interval after collecting the data, and a bolus determination module. The administration module may administer insulin continuously according to a basal profile and a bolus on demand. The bolus has a bolus amount. The data collection module may be operatively coupled to the administration module. The delay module may trigger the administration of the bolus and the data collection module may collect further data relevant for the bolus amount after the therapeutically significant delay interval ends. The delay module may trigger the administration of the bolus when an acknowledgement user input is received during the therapeutically significant delay interval. The bolus determination module may determine the bolus amount based, at least in part, on at least one of the data and the further data.

In yet another embodiment, a method for ambulatory insulin infusion may include administering insulin substantially continuously according to a basal profile and collecting a blood glucose value. The method may also include starting a therapeutically significant delay interval after the blood glucose value is collected and determining, automatically with a processor, a bolus amount of insulin based, at least in part, on the blood glucose value. The bolus amount of insulin may be administered, automatically, after the therapeutically significant delay interval expires.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
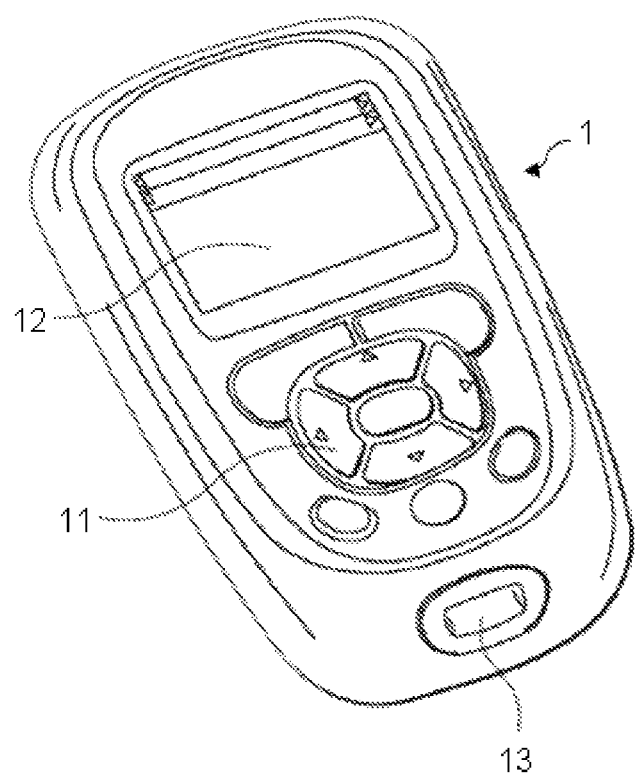
FIG. 1 schematically depicts a diabetes manager in according to one or more embodiments shown and described herein.

In the embodiments described herein, some of the steps in the procedure for programming a bolus may be carried out in advance of a situation where a bolus shall be administered.

In one embodiment, an ambulatory insulin infusion system includes an administration module for insulin administration and a data collection module for collecting data relevant for the bolus amount. The administration module may be designed to administer insulin according to a basal profile continuously and a bolus on demand. The bolus has a bolus amount. The data collection module may be operatively coupled to the administration module.

The system may further include a delay module. The delay module may trigger a start of the bolus administration a therapeutically significant delay interval after the collection of the data.

The delay module can be implemented using any combination of hardware or software. The term "software," as used herein, denotes logic or machine readable instructions written in any programming language of any generation (e.g., 1GL, 2GL, 3GL, 4GL, or 5GL) such as, for example, machine language that may be directly executed by a microcontroller, or assembly language, object-oriented programming (OOP), scripting languages, microcode, etc., that may be compiled or assembled and stored on a machine readable medium. Alternatively, the logic or machine readable instructions may be written in a hardware description language (HDL), such as implemented via either a field-programmable gate array (FPGA) configuration or an application-specific integrated circuit (ASIC), and their equivalents.

In the embodiments described herein, the delay module may be integral with general control circuitry of the system such as, for example, one or multiple microcontrollers running corresponding firmware code and supplementary circuitry. As is discussed in more detail below, the delay module may comprise a timer that is started after the collection of the data. The timer may provide a trigger signal for triggering the start of the bolus administration upon expiry of a delay interval. Alternatively, the delay module may comprise circuitry or firmware code that continuously tests if a condition for terminating the delay interval is met and provides a trigger signal upon the condition being met. A condition for terminating the delay interval may be given by the reception of an acknowledgement user input and/or by a signal provided by a continuous glucose measurement unit.

As used herein, the term "bolus" generally refers to a meal bolus that is administered in order to compensate the intake of carbohydrates. The equivalent term "meal bolus" may be used in order to avoid any ambiguity. A bolus that is administered to lower an undesirably raised blood glucose value is explicitly referred to as "correction bolus."

The phrase "therapeutically significant delay interval" refers to a delay interval that has a non-negligible impact on the PwD's blood glucose curve. That is, the resulting blood glucose curve over time is significantly different as compared to an administration of the bolus without the delay interval. The minimum length of a delay interval to be therapeutically significant is typically on the order of minutes. The minimum length may be dependent upon the PwD and the absorption characteristics of the insulin formulation. A delay on the order of seconds such as, for example, the delay between the programming of a bolus by the PwD and the beginning of its administration, is not considered as therapeutically significant as a delay on the order of minutes.

In the embodiments described herein, the administration module and the data collection module may be separate physical units having separate housings. The unit including the administration module is referred to as the "insulin pump" and the unit including the data collection module is referred to as the "diabetes manager." The system may alternatively be provided in form of a single device with a single housing or include a larger number of separate devices.

According to the embodiments described herein, a bolus may be programmed (e.g., in accordance with the general procedure for programming a bolus) at a place and time that is convenient for the PwD some time prior to the meal while the actual administration is performed later on at the end of the delay interval. Thus, the probability of complications such as hyperglycemic episodes may be reduced.

The PwD can, for example, perform a blood glucose measurement and further operational steps, as described above, in the office prior to going to lunch or in the restroom of a restaurant after ordering the meal. Thereafter, the bolus is administered when actually required, i.e., when the user actually sits down for lunch or the meal is actually served in the restaurant.

In some embodiments, the system includes a bolus determination module. The bolus determination module determines the bolus amount based, at least in part, on the collected data.

Collected data includes data relevant for a bolus amount such as a carbohydrate amount, relative amounts of fat, carbohydrates and proteins, information about a potential sickness which tends to increase the insulin demand, the amount and/or level of physical activity which tends to reduce the insulin demand, and the like.

The bolus amount may be determined when all required or desired data are collected. In one embodiment, the system includes an insulin pump and a diabetes manager. The bolus determination module may be included in the diabetes manager. The determined bolus amount and further data required for the administration may be subsequently transmitted to the insulin pump.

As is discussed below, some data may only be available at the time when the bolus is administered. In some embodiments, the diabetes manager does not need to be present when the bolus is administered at the end of the delay interval. Therefore, the data collection module may, fully or in part, be integral with the insulin pump and the bolus determination unit may, fully or in part, be integral with the insulin pump.

In some embodiments including a bolus determination module, the data collection module includes a user interface. The user interface is designed to collect meal characterizing data from a PwD. The bolus determination module is designed to determine the bolus amount based, at least in part, on the meal characterizing data. The meal characterizing data may be entered directly or recalled from a food database, i.e., the food database stores meal characterizing data for a variety of meals. In some embodiments, a diabetes manager and an insulin pump are separate physical devices which are operatively coupled. The user interface may be provided on either or both of the separate physical devices. The user interface may include pushbuttons and a display, a touch screen, a track ball, a voice recognition unit, or the like.

Time-varying and/or patient-dependent parameters, such as carbohydrate factors stored by the bolus determination module, may be needed to determine the bolus amount. For a delayed bolus administration, such parameters may be considered either for the time of day when the determination is carried out or for the time of day when the bolus is administered.

In the embodiments described herein, the user interface may be designed for direct entry of the bolus amount, e.g., as a numeric value entry or via scroll buttons. In such cases, the collected data are identical with or comprise the bolus amount.

In some embodiments, the data collection module includes a blood glucose measurement module. The bolus determination module may be designed to determine the bolus amount based, at least in part, on a blood glucose value measured by the blood glucose measurement module. Reducing the bolus amount is favorable if the current blood glucose value is particularly low. In contrast, increasing the bolus amount is favorable if the blood glucose value is particularly high. The blood glucose measurement module may, for example, be a strip-based optical or electrochemical measurement module, or a continuous blood glucose meter.

In some embodiments, the bolus determination module is designed to determine, based on a measured blood glucose value, a correction bolus amount of a correction bolus. The administration module may be designed to trigger a start of correction bolus administration without therapeutically significant delay. Since a correction bolus is administered in order to lower an undesirably raised glucose value, it may be administered immediately after being determined without a preceding delay interval. Alternatively, the correction bolus may be administered along with the meal bolus after the delay interval.

In some embodiments, the delay module is designed to trigger the start of the bolus administration after a pre-defined time interval, the pre-defined time interval defining the delay interval. After termination of the delay interval, the administration may be carried out automatically without further user input or after some further user input as is discussed below.

Embodiments utilizing pre-defined intervals may be useful if the appropriate delay interval is known when the data relevant for a bolus amount are collected by the system. For example, if a PwD goes to lunch knowing there is a constant or negligible time before the PwD will begin eating. The length of the pre-defined time interval may be entered via a user interface (e.g., when performing the steps of measuring the blood glucose value, providing food characterizing data, and the like). The length of the pre-defined time interval may be selected from a list of pre-defined delay intervals or may be a fixed time interval. While there are no fixed limits for longest or shortest delay interval, a relatively short delay interval may, for example, be in the range of about 5 minutes to about 10 minutes and a relatively long delay interval may, for example, be in the range of about 30 minutes to about 2 hours. When the bolus administration is triggered after a pre-defined delay interval, the delay module may comprise a corresponding delay timer that is started following the data collection.

In some embodiments, the delay module is designed to receive, in the delay interval, an acknowledgement user input. The delay module may trigger the start of the bolus administration upon receipt of the acknowledgement user input. Acknowledgement user input may be useful when the appropriate delay interval is not known in advance. In a restaurant, for example, the waiting time may vary considerably and be difficult to estimate in advance. A PwD may carry out all or most of a bolus programming procedure in advance (e.g., in a discrete way) and initiate the bolus administration only on demand. The acknowledgement user input may be carried out by a single key press in a discrete way, since no complex action such as watching a display or entering numeric values is required. In embodiments including separate devices, the input device for providing the acknowledgement user input may be included with any of the devices. In some embodiments, the administration module, e.g., an insulin pump, comprises the input device, since it is frequently carried by the PwD. The input device, e.g., a push button, may be designed for tactile input, e.g. through clothes. As is described below in more detail, the system may remind (e.g., once, multiple times or repeatedly) the PwD about the active delay interval in intervals of, e.g., about 1 minute or about 3 minutes.

The system may include or be operatively coupleable to further electronic devices, such as a cell phone or a smart phone (e.g., via a Bluetooth RF interface). In this case, a user interface of a further electronic device may be used for providing the acknowledgement user input and subsequently transmitted to the insulin pump or diabetes manager.

In some embodiments, the start of the bolus administration may be triggered upon reception of an acknowledgement user input. The delay module may be designed to cancel a running delay interval without triggering the bolus administration if a maximum delay interval has expired without reception of the acknowledgement user input.

For example, if the PwD is disrupted by a colleague before going to lunch with a temporally long discussion, the blood glucose measurement may become a wrong basis for calculating a meal bolus amount. Hence, if the user acknowledgement input is not provided within a predefined time interval of, for example about 30 minutes or about 45 minutes, the delay interval may be cancelled to prevent bolus administration. The blood glucose measurement may then be repeated or recalculated.

Alternatively, the delay interval may not be cancelled in such a situation. For example, an optical, acoustic and/or tactile signal may indicate that a long delay has occurred. Upon receiving the signal, the PwD can decide if the meal bolus is to be administered. If the PwD did have an intensive physical activity since the blood glucose measurement, the measurement may be repeated. If no exceptional activities were performed since the last blood glucose measurement, the PwD may decide not to repeat the measurement and administer the meal bolus even though the delay interval has exceeded a maximum delay interval.

In some embodiments, the system includes an alert module that generates an alert while the alert interval is running and/or when the delay interval is terminated.

The alert may comprise any of an acoustical, an optical or a tactile signal. Tactile signals allow the alert to be especially discrete. The administration module may include the alert module, since the administration module is commonly carried by the PwD. The user may be alerted regularly, for example in intervals of between about 2 minutes and about 6 minutes while the delay interval is running.

When the administration is automatically carried out after a pre-defined delay interval, an alert may be provided when the delay interval is terminated. The alert may serve as confirmation for the PwD that the bolus is to be administered. Optionally, the PwD may prevent the bolus administration, for example, in a situation where the PwD is hindered from consuming the meal.

In some embodiments, the delay module can be selectively disabled (e.g., set to a disabled mode), which may be suited for PwDs who require or wish a delayed bolus administration only occasionally. In some embodiments the delay module may be explicitly disabled, or the delay interval may be set to zero. Enabling or disabling the delay module may be carried out by the user, e.g., along with providing food characterizing data and/or measuring the blood glucose value as described above.

In some situations, information required for determining the bolus amount may be available only contemporaneously with the bolus administration. For example, such data may relate to the size of the meal, or a larger or smaller portion of the meal is consumed than expected. The PwD may change the input to correspond to meal alterations, for example, if a salad is served instead of a soup.

In some embodiments, the system is designed to receive, at the end of the delay interval, further data relevant to the determination of the bolus amount. The bolus amount may be determined, at least in part, based on the further data. The further data may be new data and/or an adjustment of previously entered data.

The further data relevant for the determination of the bolus amount can be entered using the diabetes manager and/or the insulin pump. The diabetes manager may be used when a large amount of data such as different meal types and/or meal sizes have to be entered, as the diabetes manager usually has a comfortable user interface. The insulin pump may be used when a small amount of data has to be entered, since the insulin pump does not require carrying the diabetes manager.

In embodiments operatively coupled to another electronic device such as a cell phone, the system may be designed such that the other device can be used for inputting the further data.

A bolus determination unit may be included, fully or in part, in the insulin pump when further data is provided at the end of the delay interval. The inclusion of the bolus determination unit, at least in part, in the insulin pump may be utilized with computation parameters such as carbohydrate ratios. Specifically, the computation parameters may be considered at the time when the administration is carried out and the delay interval is not known in advance.

In some embodiments, the system comprises multiple separate devices (e.g., a separate insulin pump and a separate diabetes manager) with the delay module arranged in the same device as the administration module. In such embodiments, no communication of the insulin pump with other units or devices is required when the delay module terminates the delay interval and the bolus is administered. Alternatively, the delay module may be integral with another device such as the diabetes manger. In such embodiments, the diabetes manager transmits a corresponding signal to the insulin pump at the end of the delay interval to cause the insulin pump to start the bolus administration.

In some embodiments, the system includes or is operatively coupleable to a continuous glucose monitoring unit. Thus, the system can be designed to take into account blood glucose values measured at the beginning, during and/or at the end of the delay interval for determining the bolus amount.

Continuous glucose measurement devices may be used by PwDs in order to control their blood glucose level. Such devices may be integrated with or operatively coupled to a system in accordance with the embodiments described herein. In some embodiments the blood glucose value is considered for determining the bolus amount. Thus, the readings of a continuous measurement system may be used in addition or alternatively to a glucose measurement before the start of the delay interval to allow the consideration of blood glucose changes in the delay interval.

A continuous glucose monitoring unit may be used to detect a blood glucose raise resulting from a carbohydrate intake. The delay module may be configured to trigger the start of the bolus administration upon the detection of the blood glucose raise. This type of embodiment is an alternative to providing a manual acknowledgement user input as described above. Carbohydrate intake is associated with a blood glucose increase and may be utilized for triggering the start of the bolus administration.

The embodiments described herein may be utilized by individuals who suffer from gastroparesis. Such individuals may administer a meal bolus with some patient-specific delay as compared to the food intake. Such delayed administration may be occasionally forgotten. According to the embodiments described herein, the delay interval may be used to delay the administration as required by the treatment of gastroparesis. For example, automatic administration after termination of a pre-defined delay interval, as described above, may be utilized. If a PwD is suffering from gastroparesis and desires an additional delay interval for discreetness reasons, the corresponding delay interval may be added. An alert at the termination of the delay interval may not be necessary and/or desirable for the treatment of gastroparesis.

In some embodiments, the delay module is designed to store a minimum delay interval. The minimum delay interval defines a lower limit for the length of the delay interval. The minimum delay interval may be defined based on the requirements of the PwD's gastroparesis.

A minimum delay interval may be implemented in different ways. For example, a single delay timer as described above may be present in the delay module with a pre-set minimum delay interval. Alternatively, a first delay timer for the minimum delay interval and a second delay timer for a further delay interval may be provided. The termination of the first delay interval may trigger the beginning of the second delay interval. In embodiments where the delay module is designed to receive an acknowledgement user input and to terminate the delay interval upon reception of the acknowledgement user input, the delay module may be designed not to accept or react on the acknowledgement user input unit termination of the minimum delay interval. Thus, a minimum delay in accordance with gastroparesis requirements may be ensured.

FIG. 1 schematically depicts a diabetes manager 1 in accordance with the embodiments described herein. The diabetes manager 1 includes a keypad 11, a display 12, and a blood glucose measurement module with a test strip socket 13. The diabetes manager 1 may include one or multiple microcontrollers running software (e.g., a corresponding firmware code) as well as supplementary circuitry.

Figure 2:
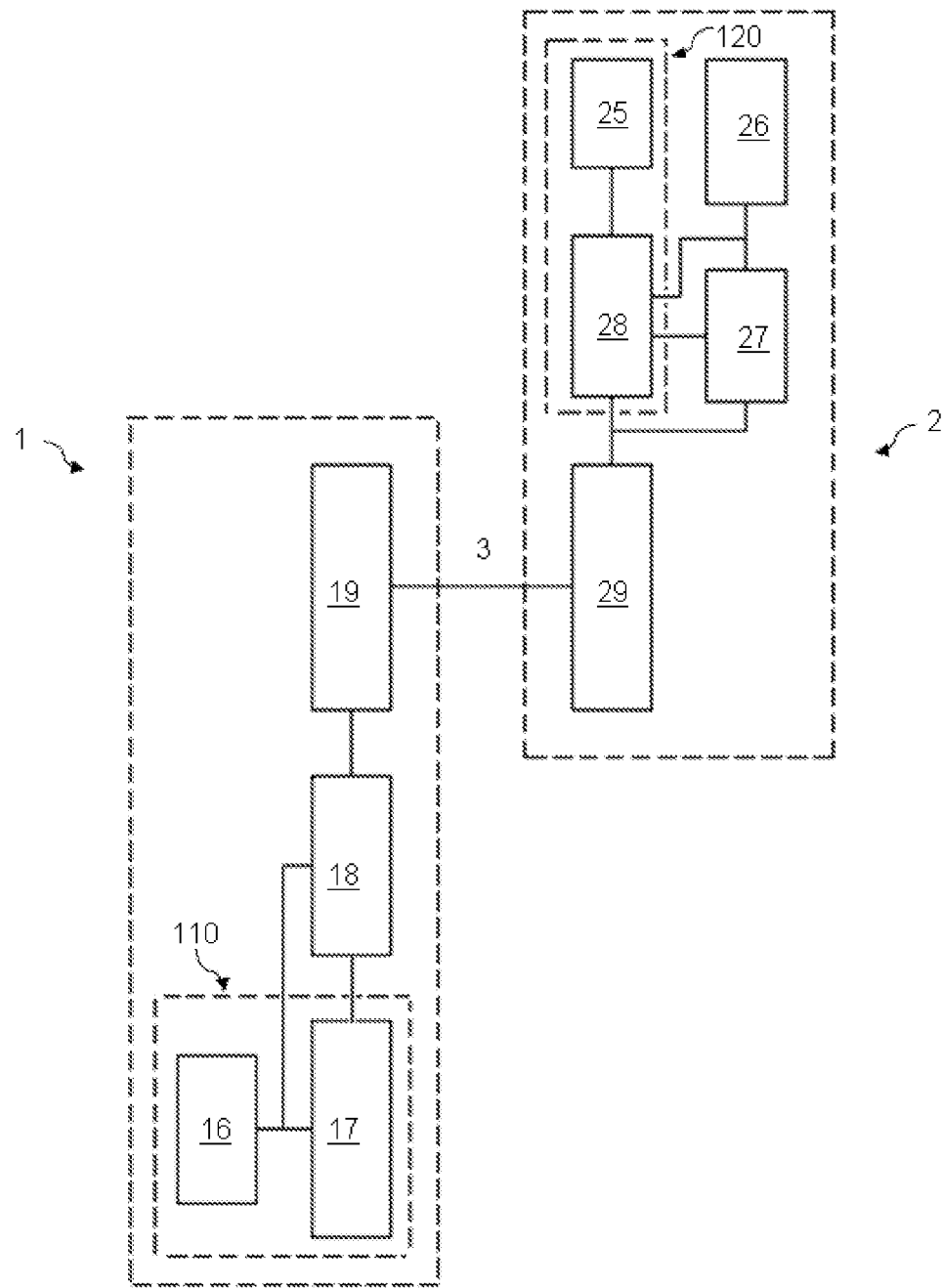
FIG. 2 schematically depicts the major units and the architecture of a system including a diabetes manager and an insulin pump according to one or more embodiments shown and described herein.

FIG. 2 schematically depicts a block diagram of an insulin infusion system 100 including a diabetes manager 1 and an insulin pump 2.

Referring collectively to FIGS. 1 and 2, the user interface 16 of the diabetes manager 1 comprises the display 12 and the keypad 11. In some embodiments, the user interface 16 comprises an optional acoustic and/or tactile indictor (not depicted). The blood glucose measurement module 17 is typically a strip-based electrochemical or optical blood glucose measurement module. In one embodiment, the data collection module 110 comprises the blood glucose measurement module 17 and the user interface 16.

The diabetes manager 1 further comprises a bolus determination module 18 that determines meal bolus amounts. In some embodiments, the bolus determination module determines correction bolus amounts based on the collected data, as is described above.

The insulin pump 2 includes an administration controller 28, a delay module 27, a user interface 26, and a pump module 25. The administration module 120 comprises the administration controller 28 and the pump module 25. The user interface 26 may include a display, a number of input units such as keys and an alert module with an acoustic and/or a tactile indicator, such as a pager vibrator.

Both the diabetes manager 1 and the insulin pump 2 additionally comprise control circuitry (not depicted) such as a microprocessor and memory. As used herein, "microprocessor" means an integrated circuit, a microchip, a computer, or any other computing device capable of executing machine readable instructions. The memory may be RAM, ROM, a flash memory, a hard drive, or any device capable of storing machine readable instructions. It is noted that the embodiments described herein may comprise distributed computing devices. Specifically, multiple autonomous processors and multiple autonomous memories may be communicably coupled and configured to cooperate in a manner analogous to the single microprocessor and single memory embodiments. Some of the modules shown in FIG. 2, such as the bolus determination module 18, the administration controller 28, and the delay module 27 may be realized, fully or in part, as integral with the control circuitry and may be implemented by software.

Both the diabetes manager 1 and the insulin pump 2 comprise corresponding communication interfaces 19 and 29 for establishing a communication channel 3 between the devices. The communication interfaces are typically designed for wireless communication over a distance up to about 1 meter to about 3 meters and are designed, for example, as an IR or Bluetooth RF interfaces.

Either or both of the communication interfaces may further be used for data exchange and/or communication with further devices, such as a cell phone or a PC.

Via the communication channel 3, the diabetes manager 1 can transmit data to the insulin pump 2 like a bolus amount to be administered and further data or commands for remotely controlling the insulin pump 2. In the other direction the insulin pump 2 (e.g., administration device) may transmit an effectively administered bolus amount along with a time stamp to the diabetes manager 1, e.g. for confirmation and record-keeping purposes. Further data may be transmitted between the diabetes manager 1 and the insulin pump 2 (e.g., administration device) as needed.

Figure 3:
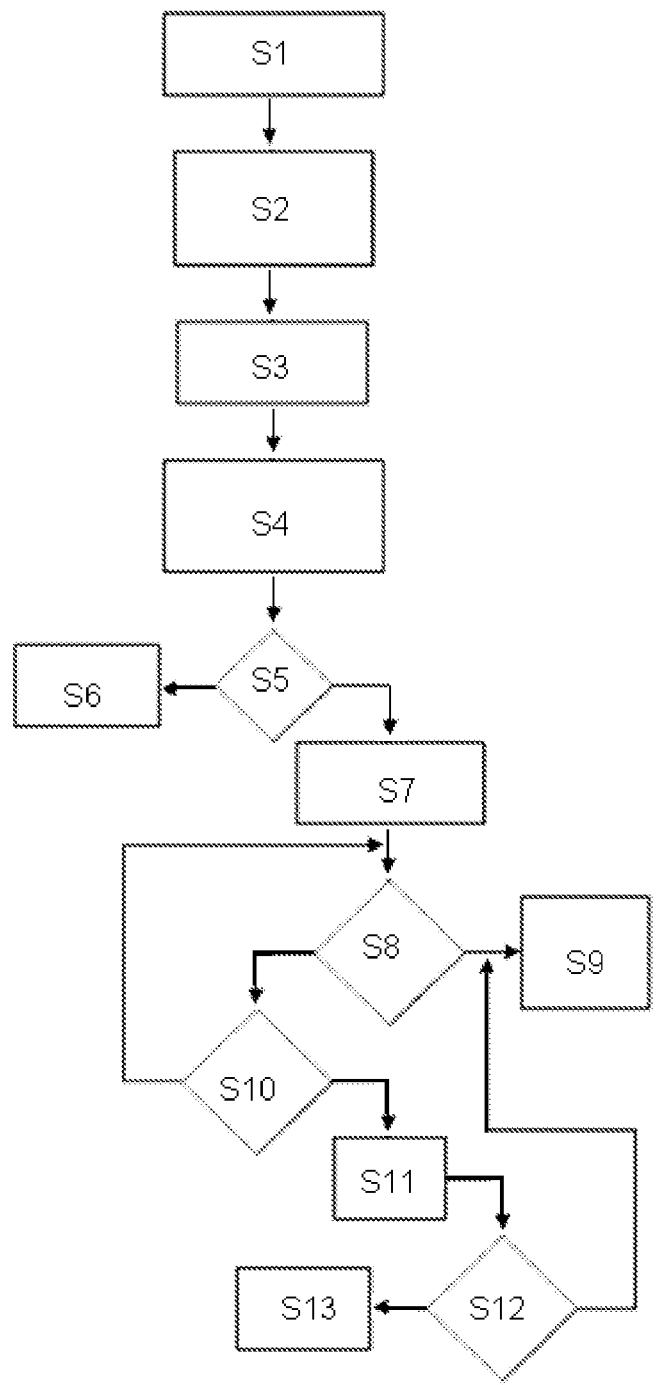
FIG. 3 schematically depicts an operational flow diagram for a bolus administration according to one or more embodiments shown and described herein.

FIG. 3 schematically depicts steps of the operational flow for a bolus administration according to an embodiment of the present disclosure.

Referring collectively to FIGS. 2 and 3, in step S1, a blood glucose measurement is taken using the blood glucose measurement module 17 and the user interface 16. While generally recommended, the blood glucose measurement is not required. The measured value may be categorized into situations like "before meal" or "after meal," as is explained above (but not depicted in FIG. 3).

In step S2, meal characterizing data with respect to a meal (e.g. a meal a PwD is planning to eat) is entered. The data may include the meal size and the amount of carbohydrates. The data may include further data such as the fat and protein content. The entry of these data may be simplified by a food database (not shown) accessible to the diabetes manager 1 (e.g., stored in memory or communicably coupled).

An administration profile for the administered bolus amount as a function of time may be selected in order to compensate for different food compositions. For example, the amount of fat and protein can have a considerable influence on the carbohydrate absorption rate. If the diabetes manager 1 includes a food database, this information may be stored along with the food type in the database. The default setting may be administration in a substantially continuous way over a short time period.

Rather than entering data with respect to food in step S2, the bolus amount may be directly entered. Thusly, a PwD may directly set a desired bolus amount.

Based on the food entry data, a bolus amount entered directly, or a measured blood glucose value, the bolus determination module 18 determines the bolus amount to be administered in step S3. The bolus amount may include two components: a correction bolus amount for lowering an undesirably raised blood glucose value, and a meal bolus amount for compensating for the coming meal intake.

The determined bolus amount may be displayed, for example using the display 12 of diabetes manager 1. Thus, a PwD may adjust the determined bolus amount to a desired value if the determined bolus amount is inappropriate for any reason.

In addition to the blood glucose value and/or the meal characterizing data, the determination may consider additional factors such as the amount of currently active insulin in the PwD's body (Insulin on Board), resulting from prior administrations.

In addition to the data described above, a decision whether the bolus shall be administered immediately or after a delay interval may be entered via the user interface 16.

Data required by the insulin pump 2 for carrying out the administration are transmitted via the communication channel 3 from the diabetes manager 1 to the insulin pump 2 in step S4.

The steps S1 to S4 may be carried out by the PwD in a private environment, for example, in the office or a restaurant restroom. After the data transmission in step S4, the diabetes manager 1 is not required for the subsequent steps. Thus, the diabetes manager 1 is not needed, e.g., the diabetes manager 1 may be left and not be taken along to where the meal is to be served.

After the data is transmitted from the diabetes manager 1 to the insulin pump 2, the steps subsequent to step S5 depend upon whether the meal bolus is to be administered immediately or delayed. For immediate administration, the delivery of both the meal bolus and possibly a correction bolus is carried out immediately in step S6. For example, if the PwD is at home and special discreetness is not required.

If the meal bolus is to be administered after a delay interval, a correction bolus may be administered without delay in step S7 because the insulin for correcting a raised glucose value is generally administered as soon as possible. The following operational steps are carried out under control of the delay module 27.

In step S8, it is determined if the delay interval is to be terminated and/or the bolus administration is to be triggered. Administration of the meal bolus may be triggered via the user interface 26 of the insulin pump 2. For example, a single key press that provides the acknowledgement user input for triggering the start of the administration. The acknowledgement user input may also be provided via the diabetes manager 1. The acknowledgement user input may then be transmitted from the diabetes manager 1 to the insulin pump 2 via the communication channel 3. Reception of the acknowledgement user input may be notified, e.g., by an acoustic and/or tactile indication, via the user interface 26 of the administration device. In step S9, the administration of the bolus amount is carried out by the pump module 25 under control of the administration controller 28.

If the administration is not triggered and the delay interval is accordingly not terminated, in an optional step S10 it is determined if a timeout has occurred, i.e., if a maximum delay interval has expired. The maximum delay interval may be a user-selectable parameter and/or may be a preset value. The maximum delay interval may be in a range of about 30 minutes to about 180 minutes such as, for example, a maximum delay interval of about 45 minutes to about 60 minutes. Other values, however, may be used as well. The maximum delay interval ensures that a meal bolus is not administered if the general circumstances have considerably changed as compared to the time of its determination, as is explained above.

If a timeout occurs, an alert may be provided in step S11 via the alert module of the user interface 26. After the alert, a decision is made whether to immediately trigger the bolus administration in step S12. In this case, the administration is carried out in step S9. This situation may occur, for example, if the PwD forgets to actually trigger the administration when eating a meal. If the administration is not triggered in step S12, the delay interval is canceled in step S13. Alternatively, the operational flow may directly proceed with step S13 and cancel the delay interval in the case of a timeout.

If no timeout is detected in step S10, the operational flow proceeds with step S8. In this case, the steps S8 and S10 are carried out in a continuous cycle as long as no acknowledgement user input is provided and no timeout has occurred.

Figure 4:
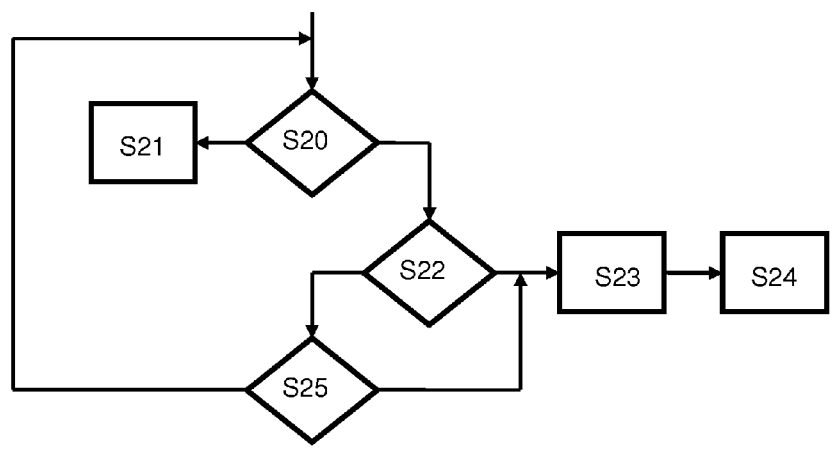
FIG. 4 schematically depicts an operation flow diagram for a bolus administration according to one or more embodiments shown and described herein.

FIG. 4 illustrates the operational flow for a further embodiment. For the general architecture of the system of this embodiment, reference is made to FIG. 2.

For the embodiment depicted in FIG. 4, the first steps of the operational flow (depicted as a downward pointing arrow in FIG. 4) may be identical to steps S1 to S7 schematically depicted in FIG. 3, as described herein. In addition to entering food characterizing data and/or further data relevant for the bolus amount, a time interval may be entered via the user interface 16 or selected from a list. The time interval subsequently serves as pre-defined delay interval. The delay interval may be zero in situations with an administration without delay.

FIG. 4 schematically depicts operational steps following step S7 of FIG. 3. In step S20, a determination is made whether the delay interval should be cancelled. Canceling the delay interval may be carried out via a corresponding user input through the user interface 26 of the insulin pump 2 (FIG. 2). The delay interval may also be carried out via a user input on the user interface 16 of the diabetes manager 1 or via a user input on a further device, such as a cell phone operatively coupled to the system via either of the communication interfaces 19, or 29 or a further communication interface. If the delay interval is cancelled, the operational flow for the bolus administration is terminated in step S21 without the administration being carried out. As described above, the option for cancelling the delay interval may be useful in situations where a PwD, for some reason, does not whish the bolus to be administered.

If the delay interval is not canceled in step S20, a determination is made in step S22 whether the delay interval has been manually terminated to trigger the administration, even though the fixed delay interval has not yet expired. This option may be useful in a situation where the delay interval has been programmed, but needs to be cancelled. For example, if a delay interval is set in accordance with past experience with a restaurant, but the meal is served earlier than expected. In an analogue to canceling the delay interval and preventing the bolus administration, the user input for carrying out the administration may be provided via either of the user interfaces 16, 26 of the diabetes manager 1 or the insulin pump 2, respectively, or via a further external device.

If it has been determined that the administration should be carried out, further data that are relevant for determining the bolus amount or adjust previously provided data is entered in step S23. If further data are provided or adjusted, step S23 further includes determining an updated bolus amount. The updated bolus amount may be determined by a bolus determination unit in the insulin pump 2 or the bolus determination module 18 of the diabetes manager 1. The bolus determination unit of the insulin pump 2 may offer the same functionality as the bolus determination module 18 of the diabetes manager 1. It may, however, also offer different or limited functionality relative to the bolus determination module 18 of the diabetes manager 1. Determining correction bolus amounts, for example, may be carried out only by the bolus determination module 18 of the diabetes manager 1 in some embodiments.

In a further embodiment, the diabetes manager 1 does not include a bolus determination unit and the bolus determination is performed by the insulin pump 2. For this type of embodiment, meal characterizing and further data as described above are transmitted from the diabetes manager 1 to the insulin pump 2 rather than a bolus amount.

In step S4, the bolus administration is triggered.

If the delay interval is not terminated in step S22, a determination is made in step S25 whether the pre-defined delay interval has expired. In this case, the operational flow continues with the potential entry of further data in step S23 and the administration in step S24. Otherwise, the operational flow continues with step S20.

For example, the steps S20, S22, and S25 may be carried out in a continuous cycle unless the delay interval is canceled or manually terminated via a user input or the pre-defined delay interval has expired.

It is noted that some or all of the steps S20, S21, S22, S23 depicted in FIG. 4 may, fully or partly, be omitted. For example, step S25 of testing if the fixed delay interval has terminated may be carried out continuously with the administration triggered in step S24 once the condition is fulfilled.

In a further embodiment, the bolus determination module 18 is omitted and the bolus amount of a bolus to be administered is directly entered.

In the described embodiments, the diabetes manager 1 and the insulin pump 2 are separate devices. This separation, however, is not essential. Data entry and determination of the bolus amount may be carried out directly on the insulin pump 2. Additionally it is noted that any steps, inputs, or actions described herein as being performed by a PwD may be performed, for example, by any individual or automatically with a processor.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and the scope of the claimed subject matter. Thus it is intended that the specification cover the modifications and variations of the various embodiments described herein provided such modifications and variations come within the scope of the appended claims and their equivalents.

What is claimed is:

1. An ambulatory insulin infusion system, comprising:
   an administration module for insulin administration, wherein the administration module administers insulin continuously according to a basal profile and a bolus on demand, the bolus having a bolus amount;
   a data collection module for collecting data relevant for the bolus amount, wherein the data collection module is operatively coupled to the administration module; and
   a delay module operatively coupled to the administration module and the data collection module, wherein the delay module triggers administration of the bolus automatically by the administration module upon expiry of a therapeutically significant delay interval started by the delay module after the data is collected by the data collection module, wherein the delay module is designed to also trigger the administration of the bolus in the delay interval upon receipt of an acknowledgment user input.

2. The ambulatory insulin infusion system of claim 1 further comprising a bolus determination module that determines the bolus amount based, at least in part, on the data.

3. The ambulatory insulin infusion system of claim 2, wherein the data collection module comprises a blood glucose measurement module that measures a blood glucose value and the bolus determination module determines the bolus amount based, at least in part, on the blood glucose value measured by the blood glucose measurement module.

4. The ambulatory insulin infusion system of claim 3, wherein the bolus determination module determines a correction bolus amount of a correction bolus based on the blood glucose value measured by the blood glucose measurement module, and the administration module triggers a correction bolus administration.

5. The ambulatory insulin infusion system of claim 2, wherein the data collection module comprises a user interface that collects meal characterizing data, and the bolus determination module determines the bolus amount based, at least in part, on the meal characterizing data.

6. The ambulatory insulin infusion system of claim 1, wherein the therapeutically significant delay interval is a pre-defined time interval.

7. The ambulatory insulin infusion system of claim 1, wherein the delay module terminates a running delay interval without triggering the administration of the bolus when a maximum delay interval has expired without receipt of the acknowledgement user input.

8. The ambulatory insulin infusion system of claim 1 further comprising an alert module that generates an alert during the therapeutically significant delay interval and/or when the therapeutically significant delay interval is terminated.

9. The ambulatory insulin infusion system of claim 1, wherein the delay module has a disabled mode.

10. The ambulatory insulin infusion system of claim 1, wherein the ambulatory insulin infusion system receives further data that is relevant for a determination of the bolus amount at an end of the therapeutically significant delay interval and determines the bolus amount, at least in part, based on the further data.

11. The ambulatory insulin infusion system of claim 1, wherein the administration module and the data collection module are located in separate housings.

12. The ambulatory insulin infusion system of claim 11, wherein the delay module and the administration module are located in a same housing.

13. The ambulatory insulin infusion system of claim 1, wherein the ambulatory insulin infusion system is operatively coupled to a continuous glucose monitoring unit that measures a blood glucose value at one or more of a beginning of the therapeutically significant delay interval, during the therapeutically significant delay interval, and at an end of the therapeutically significant delay interval, and the bolus amount is determined based, at least in part, on the blood glucose value.

14. The ambulatory insulin infusion system of claim 1, wherein the delay module stores a minimum delay interval that is a lower limit for a length of the therapeutically significant delay interval.

15. An ambulatory insulin infusion system, comprising:
an administration module for insulin administration, wherein the administration module administers insulin continuously according to a basal profile and a bolus on demand, the bolus having a bolus amount;
a data collection module;
a delay module operatively coupled to the administration module and the data collection module and which is configured to start automatically a therapeutically significant delay interval after collecting the data by the data collection module, wherein the delay module triggers the administration of the bolus and the data collection module collects further data relevant for the bolus amount after the therapeutically significant delay interval ends, and the delay module also triggers the administration of the bolus by the administration module upon receipt of an acknowledgement user input during the therapeutically significant delay interval; and
a bolus determination module that determines the bolus amount based, at least in part, on at least one of the data and the further data.

16. A method for ambulatory insulin infusion, comprising:
administering insulin substantially continuously according to a basal profile via an administration module;
collecting a blood glucose value via a data collection module;
starting automatically a therapeutically significant delay interval after the blood glucose value is collected via a delay module;
determining, automatically with a processor that is operatively coupled to the administration module, the data collection module and the delay module, a bolus amount of insulin based, at least in part, on the blood glucose value received from the data collection module;
administering, via the administration module, the bolus amount of insulin, automatically, upon one of: after the therapeutically significant delay interval expires, and receipt of an acknowledgement user input during the therapeutically significant delay interval.

17. The method of claim 16 further comprising:
receiving further data relevant to the bolus amount of insulin after the therapeutically significant delay interval expires, wherein the bolus amount of insulin is based, at least in part, on the further data.

18. The method of claim 16 further comprising:
determining a correction bolus amount of insulin based on the blood glucose value; and administering the correction bolus amount substantially immediately after the correction bolus amount is determined.

* * * * *

UNITED STATES PATENT AND TRADEMARK OFFICE
CERTIFICATE OF CORRECTION

PATENT NO. : 9,629,957 B2
APPLICATION NO. : 12/969664
DATED : April 25, 2017
INVENTOR(S) : Reto Sigrist et al.

Page 1 of 1

It is certified that error appears in the above-identified patent and that said Letters Patent is hereby corrected as shown below:

On the Title Page

(75) Inventors: "Reto Sigrist, Golaten (CH);
Nicole Bernini, Burgdorf (CH);
Axel Remde, Luetzelflueh (DE)"

Should read:
(75) Inventors: --Reto Sigrist, Golaten (CH);
Nicole Bernini, Burgdorf (CH);
Axel Remde, Luetzelflueh (CH)--

Signed and Sealed this
Twentieth Day of February, 2018

Andrei Iancu
*Director of the United States Patent and Trademark Office*